United States Patent
Kantor

(10) Patent No.: US 6,923,788 B2
(45) Date of Patent: Aug. 2, 2005

(54) CATHETER HAVING A LOW-FRICTION GUIDEWIRE LUMEN AND METHOD OF MANUFACTURE

(75) Inventor: John D. Kantor, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 0 days.

(21) Appl. No.: 10/667,609

(22) Filed: Sep. 23, 2003

(65) Prior Publication Data

US 2004/0127849 A1 Jul. 1, 2004

Related U.S. Application Data

(63) Continuation-in-part of application No. 10/226,340, filed on Aug. 23, 2002, now Pat. No. 6,849,062.

(51) Int. Cl.[7] ................ A61M 31/00; A61M 37/00; A61M 5/178; A61M 25/01; A61M 25/02
(52) U.S. Cl. .................. 604/103.04; 604/103.09; 604/164.13; 604/528
(58) Field of Search .................. 604/96.01, 103.04, 604/103.09, 164.13, 264–266, 523–528; 606/191–195; 600/431, 433–435

(56) References Cited

U.S. PATENT DOCUMENTS

| | | | |
|---|---|---|---|
| 4,406,656 A | 9/1983 | Hattler et al. | |
| 4,601,713 A | 7/1986 | Fuqua | |
| 4,668,221 A | 5/1987 | Luther | |
| 4,700,693 A | 10/1987 | Lia et al. | |
| 5,032,113 A | 7/1991 | Burns | |
| 5,163,906 A | 11/1992 | Ahmadi | |
| 5,325,845 A | 7/1994 | Adair | |
| 5,411,479 A | * 5/1995 | Bodden | 604/101.03 |
| 5,607,404 A | 3/1997 | Khairkhahan | |
| 5,800,414 A | 9/1998 | Cazal | |
| 5,891,111 A | 4/1999 | Ismael | |
| 2004/0059291 A1 | * 3/2004 | McDonnell et al. | 604/103.04 |

* cited by examiner

Primary Examiner—Nicholas D. Lucchesi
Assistant Examiner—Catherine S. Williams

(57) ABSTRACT

A catheter shaft for a catheter includes a centrally-located guidewire lumen. A body portion of the catheter shaft includes arc-shaped nodes that define a guidewire track within the guidewire lumen. The nodes include a crown region that includes a single contact point for the guidewire and may be formed of a material having a lower coefficient of friction. At least one node has an inflation lumen extending therethrough. The catheter shaft has a cut in it extending radially from the guidewire lumen to an exterior surface of the catheter shaft. The balloon catheter has a guide member that opens the cut and tracks the guidewire in and out of the catheter shaft along a length of the catheter shaft which is cut.

24 Claims, 11 Drawing Sheets

CATHETER HAVING A LOW-FRICTION GUIDEWIRE LUMEN AND METHOD OF MANUFACTURE

BACKGROUND OF THE INVENTION

1. Field of the Invention

This invention relates generally to a medical device. More specifically, the invention relates to a catheter for insertion over a guidewire through a patient's vasculature, the catheter having a low friction guidewire lumen.

2. Background of the Invention

Cardiovascular disease, including atherosclerosis, is the leading cause of death in the U.S. The medical community has developed a number of methods and devices for treating coronary heart disease, some of which are specifically designed to treat the complications resulting from atherosclerosis and other forms of coronary arterial narrowing.

One method for treating atherosclerosis and other forms of coronary narrowing is percutaneous transluminal coronary angioplasty, commonly referred to as "angioplasty" or "PTCA". The objective in angioplasty is to enlarge the lumen of the affected coronary artery by radial hydraulic expansion. The procedure is accomplished by inflating a balloon of a balloon catheter within the narrowed lumen of the coronary artery. Radial expansion of the coronary artery occurs in several different dimensions, and is related to the nature of the plaque. Soft, fatty plaque deposits are flattened by the balloon, while hardened deposits are cracked and split to enlarge the lumen. The wall of the artery itself is also stretched when the balloon is inflated.

Conventional angioplasty guidewires typically include a proximal shaft, an intermediate section and a flexible distal tip. The proximal shaft comprises a solid wire or a solid wall tube. The shaft primarily functions to guide and support a catheter, and to smoothly transmit rotation from the proximal end to an intermediate section.

The intermediate section extends axially from the proximal shaft and generally comprises a tapered core wire surrounded by a coiled spring and typically has more flexibility than the proximal shaft. Like the proximal shaft, the intermediate section must assist in guiding the catheter and smoothly transmitting rotation. However, some degree of flexibility in the intermediate section is desirable to conform the catheter to the curvature of the aortic arch and the coronary arteries.

Extending from the intermediate section at a distal joint is the flexible distal tip that accepts a pre-formed curved shape resembling a "J". The curved tip tends to steer the guidewire in the direction of the hook.

All balloon catheters must have an inflation lumen through which a fluid can be forced to pressurize the balloon. As such, catheter typically have at least two lumens (viz., a guidewire lumen and an inflation lumen). Catheters having more than one lumen are commonly referred to as "dual-lumen" or "multi-lumen" catheters.

Multi-lumen catheters have cross-sections in a variety of shapes. FIGS. 1 and 2 are examples of prior art, dual-lumen catheter cross-sections. FIG. 1 is a cross-section of a coaxial catheter 100. Coaxial catheter 100 includes an inner tube 102 and an outer tube 104. Inner tube 102 defines an inner lumen or guidewire lumen 108 adapted to receive a guidewire 106. An annular inflation lumen 110 is defined between inner tube 102 and outer tube 104, and is in fluid communication with an interior of a dilatation balloon (not shown).

In use, a guidewire is introduced into a coronary artery and is steered by manipulation of its proximal end, while being observed under a fluoroscope, until the guidewire passes through a stenosis site in the artery. Once the guidewire is in place at the treatment site, a balloon dilatation catheter is advanced over the guidewire, being thus guided directly to the stenosis site so as to place the balloon within the stenosis. Once so placed, the balloon is inflated under substantial pressure to dilate the stenosis.

The anatomy of coronary arteries varies widely from patient to patient. Often a patient's coronary arteries are irregularly shaped and highly tortuous. The tortuous configuration of the arteries may present difficulties to the physician in proper placement of the guidewire, and advancement of the catheter to the site of the stenosis. A highly tortuous coronary anatomy typically will present considerable resistance to advancement of the catheter over the guidewire.

With some types of catheter construction, the increased resistance may cause a tendency for portions of the catheter to collapse or buckle axially. For example, in a catheter having a shaft formed from inner and outer coaxial tubes, such as is shown in FIG. 1, and a balloon mounted to the distal ends of the tubes, there may be a tendency for the tubes to "telescope" when presented with an increase in resistance. The telescoping of the tubes tends to draw the ends of the balloon together slightly, but sufficiently to permit the balloon to become bunched-up as it is forced through the stenosis. This bunching-up of the balloon makes it more difficult for the balloon to access the stenosis site.

Additionally, it is sometimes necessary for the physician to place a torque load on the guidewire in an effort to overcome resistance encountered in a vessel. A torque load applied to a coaxial catheter can cause the outer tube to twist, while the inner tube remains stationary, causing a rotation of the tubes relative to one another.

FIG. 2 shows a cross-sectional view of a non-coaxial, dual-lumen catheter 200. An inflation lumen 202 is in fluid communication with an interior of a dilatation balloon (not shown). A guidewire lumen 204 is defined at least in part by inner tubular member 206 which extends the entire length of the catheter body. A guidewire 208 is shown within guidewire lumen 204. As explained above, a catheter is slid over the guidewire through a tortuous blood vessel. Because guidewire lumen 204 is not coaxial with inflation lumen 202, the guidewire is not centrally located in catheter 200. Thus, when a torque is applied to the catheter to traverse the twists and turns of a body lumen, the catheter does not rotate smoothly. Instead the catheter has a tendency to "flip" in response to an applied torque because the center of gravity of the catheter is not centrally located within the catheter shaft.

When inserting a catheter over a guidewire, friction between the two pieces occurs whenever the guidewire contacts the wall of the catheters guidewire lumen. If both the guidewire and the guidewire lumen of the catheter have circular cross-sections with substantially equal diameters, as shown in FIGS. 1 and 2, tracking of the catheter over the guidewire is diminished due to friction between the guidewire and the catheter guidewire lumen. Further, in navigating tortuous areas of a vessel where the catheter body is often "flexed," such a guidewire lumen will deform and thereby contact a substantial portion of the outer surface of the guidewire.

Further, in some convention catheters, such as a coaxial over-the-wire catheter, a physician must push the catheter from a coaxial position primarily, such that the force is primarily applied to an outer shaft. Thus the outer shaft may become misaligned or "bunch" with respect to an inner shaft.

In a typical procedure, a physician will first insert and advance a guidewire to the stenosis site. An initial dilatation catheter having a fairly small diameter balloon is then passed over the guidewire to the site and the balloon is inflated to partially dilate the vessel. The balloon is then deflated and the catheter withdrawn. Balloon catheters having progressively larger balloons are then advanced to the stenosis along the guidewire, inflated, deflated, and then withdrawn in succession to sufficiently enlarge the lumen of the artery.

In order to accomplish the multiple dilatations, the original catheter must be removed and a second balloon catheter tracked to the lesion. When catheter exchange is desired, it is advantageous to leave the guidewire in place while the first catheter is removed in order to insert the second catheter without having to reestablish the path by inserting a new guidewire. To remove a balloon catheter while leaving the guidewire in place, there must be a portion of the guidewire extending out of the balloon catheter at the proximal end so that the guidewire can be held in place while the balloon catheter is removed.

Two types of catheters commonly used in angioplasty procedures are referred to as over-the-wire (OTW) catheters and rapid exchange (RX) catheters. A third type of catheter with preferred features of both OTW and RX catheters, that is sold under the trademarks MULTI-EXCHANGE, ZIPPER MX, ZIPPER, and/or MX is discussed below. An OTW catheter's guidewire shaft runs the entire length of the catheter and is attached to, or enveloped within, an inflation shaft. FIGS. 1 and 2 are typical of OTW catheters. Thus, the entire length of an OTW catheter is tracked over a guidewire during a PTCA procedure. A RX catheter, on the other hand, has a guidewire shaft that extends within only the distal most portion of the catheter. Thus, during a PTCA procedure only the distal most portion of a rapid exchange catheter is tracked over a guidewire.

If a catheter exchange is required while using a standard OTW catheter, the user must add an extension onto the proximal end of the guidewire to maintain control of the guidewire, slide the catheter off of the extended guidewire, slide the new catheter onto the guidewire and track back into position. Multiple operators are required to hold the extended guidewire in place while the original catheter is changed out.

A RX catheter avoids the need for multiple operators when changing out the catheter and therefore is often referred to as a "single operator" catheter. With a rapid exchange catheter, the guidewire is outside the shaft of the catheter for all but the distal most portion of the catheter. The guidewire can be held in place without an extension when the catheter is removed from the body. Once the original catheter is removed, a subsequent catheter may be threaded onto the in place guidewire and tracked to the lesion. However, one problem associated with RX catheters is that the exposed portion of the guidewire may become tangled with the catheter shaft during use.

In addition, there are instances when the guidewire and not the catheter must be replaced. For example, the guidewire may become damaged during the procedure or it may be discovered during the procedure that a different shape, length, or size of guidewire is needed. An OTW catheter, with the guidewire lumen extending the entire length of the catheter, allows for simple guidewire exchange. With a RX catheter, the guidewire lumen does not extend the entire length of the catheter. Therefore, the guidewire, and most of the catheter, must be removed from the body in order to exchange guidewires. Essentially the procedure must then start anew because both the guidewire and the catheter must be retracked to the treatment site.

A balloon catheter capable of both fast and simple guidewire and catheter exchange is particularly advantageous. A catheter designed to address this need sold by Medtronic AVE, Inc. of Santa Rosa, Calif. under the trademarks MULTI-EXCHANGE, ZIPPER MX, ZIPPER and/or MX (hereinafter referred to as the "MX catheter") is disclosed in U.S. Pat. No. 4,988,356 to Crittenden et al., incorporated in its entirety herein by reference. FIG. 7 shows an MX catheter cross sectional design as disclosed in copending U.S. application Ser. No. 10/116,234, filed Apr. 4, 2002, which is incorporated in its entirety herein by reference. The MX catheter 728 includes a catheter shaft 732 having a guidewire lumen 734 which is non-coaxial to and side-by-side with an inflation lumen 737, which is reinforced by an inner tubular member 733. A cut 730 extends longitudinally along catheter shaft 732 and radially from an interior surface 735 of guidewire lumen 734 to an outer surface 736 of catheter shaft 732. A guide member (not shown) through which catheter shaft 732 is slidably coupled cooperates with cut 730 such that a guidewire 738 may extend transversely into or out of the guidewire lumen 734 at any location along the cut 730. By moving catheter shaft 732 with respect to the guide member, the effective OTW length of the MX catheter is adjustable.

BRIEF SUMMARY OF THE INVENTION

It is among the general objects of the present invention to provide an alternative catheter which allows for simple catheter and guidewire exchanges. Specifically, the present invention is a multi-lumen catheter including both a full-length inflation lumen and guidewire lumen that is responsive to applied torque loads, without "flipping,""bunching" or having various shafts "flex" against one another. Further, the present invention has improved trackability over a guidewire due to minimal friction between the guidewire and guidewire lumen.

To achieve the foregoing and other objects, and in accordance with the purposes of the present invention as embodied and broadly described herein, the balloon catheter of the present invention provides a low-friction guidewire lumen which imparts greater strength and better trackability to the catheter. The balloon catheter of the present invention has an elongate shaft with at least one inflation lumen and a non-circular, centrally-located guidewire lumen.

In one embodiment, the guidewire lumen is formed in an essentially "star-shape" with guidewire lumen arms extending toward an outer surface of the catheter shaft. Nodes, arc-shaped portions of the catheter shaft wall that extend into and narrow the guidewire lumen, are situated on either side of the guidewire lumen arms. The nodes each have an innermost point that intersects with and forms a portion of a centrally-located guidewire track. Each guidewire lumen arm extends away from the guidewire track, between each node, to a location of minimum thickness between an outer surface of the catheter shaft and the guidewire lumen.

Each node includes a region comprising a crown, that is an innermost portion of the node, which tangentially intersects with and thereby forms the guidewire track. In one embodiment, the crown is formed of a material different than the material used to form the remaining body portion of the catheter. Accordingly, the catheter is formed of at least two materials. The material used to form the body portion of the catheter provides the requisite burst and tensile strength needed to withstand the inflation pressures and torque that the catheter is subjected to during an angioplasty procedure. Whereas the material forming the crown, in addition to have sufficient burst and tensile strength, is a material having a lower coefficient of friction than the material forming the rest of the body of the catheter. This enables smooth and easy travel over a guidewire within the guidewire lumen. Because of the arc-shape, the crown of each node contacts the guidewire at only a single point in cross-section thereby effectively creating "rolling friction" rather than "sliding friction" between the guidewire and the catheter shaft.

A balloon catheter in accordance with the present invention includes at least one guidewire lumen node having an inflation lumen formed therein which extends from a proximal end of the catheter to an inflatable balloon at the distal end thereof. The inflation lumen is in fluid communication with the balloon. The inflation lumen extends substantially parallel to the guidewire lumen, over a substantial length of the catheter.

In another embodiment of the balloon catheter of the present invention, the catheter shaft includes nodes that each have an inflation lumen formed therein, which are in fluid communication with a dilatation balloon attached thereto. An outer wall of each inflation lumen creates a convex portion on an exterior surface of the catheter shaft. Each convex portion is separated by an arc-shaped indentation, thereby reducing the total surface area of the catheter shaft in contact with a body lumen when such catheter is tracked therethrough. The guidewire lumen of this embodiment is similar to that described above except that the guidewire lumen arms are shallower, thereby increasing the catheter wall thickness.

In another embodiment of the balloon catheter of the present invention, the catheter shaft described above is incorporated into a MX catheter design. Thus, a cut extends between the guidewire lumen and an exterior surface of the catheter shaft. The cut is disposed at an apex of one of the arms of the guidewire lumen. The apex occurs where there is a minimum distance between the guidewire lumen and the exterior surface of the catheter shaft. In this embodiment, the balloon catheter has a guide member that opens the cut and tracks the guidewire in and out of the guidewire lumen of the catheter shaft along a length of the catheter shaft that includes the cut.

In order to provide additional flexibility at the distal section of the balloon catheter, another embodiment of the present invention includes the catheter design described above only on a proximal section of the balloon catheter. The distal section comprises a coaxial catheter design. A reduction in the number of lumens at the distal portion of the balloon catheter provides additional flexibility where the catheter traverses the particularly tortuous body lumens.

In this embodiment, a generally circular distal guidewire lumen is disposed coaxially inside a generally circular distal catheter shaft. A distance between the distal guidewire lumen and the distal catheter shaft defines a distal inflation lumen. The distal section is bonded to the proximal section such that the proximal inflation lumen disposed in the nodes of the previous design are fluidly connected to the distal inflation lumen and that the distal guidewire lumen and the proximal guidewire lumen are coaxially aligned. Bonding the distal guidewire lumen to the nodes of the proximal guidewire lumen helps to keep the distal guidewire lumen centered in the distal section and reduces a telescoping effect of the coaxial distal lumens.

In another embodiment, the MX catheter shaft according to the present invention, with the guide member allowing access to the guidewire lumen through the cut, is the proximal section that is attached to the distal section described above.

Further, the embodiment described above is made by extruding the separate catheter shafts and bonding the pieces together with mandrels placed in the proximal inflation lumen and the distal guidewire lumen. The mandrels keep the proximal inflation lumen and the distal guidewire lumen from melting closed.

BRIEF DESCRIPTION OF THE DRAWINGS/ FIGURES

The foregoing and other features and advantages of the invention will be apparent from the following, more particular description of preferred embodiments of the invention, as illustrated in the accompanying drawings.

DETAILED DESCRIPTION OF THE INVENTION

The preferred embodiments of the present invention are now described with reference to the figures where like reference numbers indicate identical or functionally similar elements. While specific materials and method steps are discussed, it should be understood that this is done for illustrative purposes only. A person skilled in the relevant art will recognize that other materials or method steps can be used.

Figure 2:
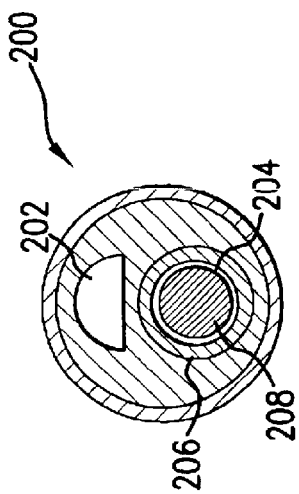
FIG. 2 is a cross-sectional view of a prior art, dual-lumen non-coaxial OTW catheter.
Figure 1:
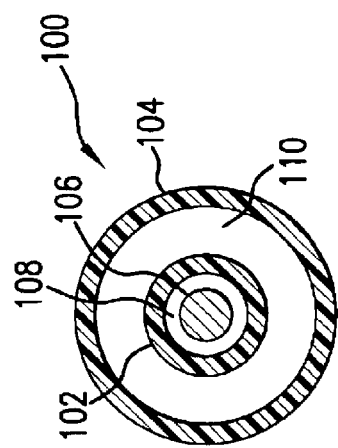
FIG. 1 is a cross-sectional view of a prior art coaxial OTW catheter.
Figure 3:
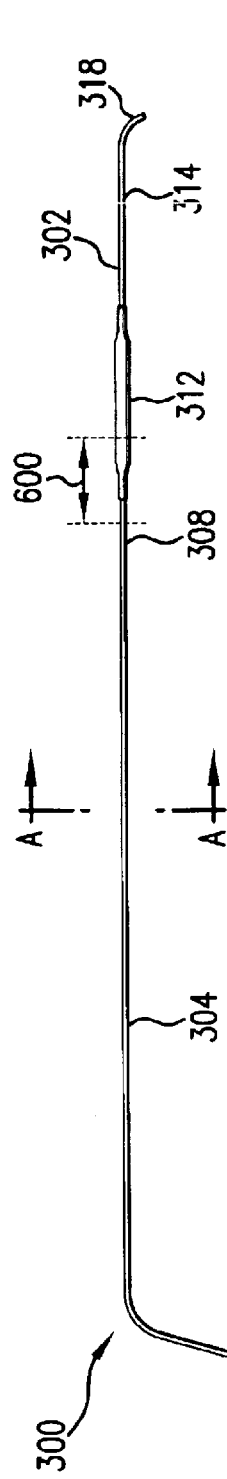
FIG. 3 is a view of an OTW balloon catheter and guidewire assembly according to the present invention.

Referring first to FIG. 3, an embodiment of a dilatation catheter 300 and a guidewire 302 are shown. Dilatation or balloon catheter 300 includes a catheter shaft 304 having a proximal end 306 and a distal end 308. Proximal end 306 of catheter shaft 304 is secured to a luer hub 310. Distal end 308 of catheter shaft 304 is attached to a dilatation balloon 312. An interior of balloon 312 is in fluid communication with an external source of inflation fluid through the length of catheter shaft 304.

Balloon 312 is formed of a thin, pliable material capable of expanding from a compact, collapsed state to an expanded diameter. Balloon 312 may be formed from polyethylene terephthalate (PET) using a drawing and blow molding process, so as to provide biaxial orientation to the material. PET balloons exhibit the desirable properties of high burst strength and relatively low radial expansion when inflated to high pressures. Alternatively, balloon 312 may be formed from polyethylene, PVC, polypropylene, polyvinyl chloride, nylon, PEBAX or other material, as would be apparent to one skilled in the relevant art. Balloon 312 may be about 8 mm to about 35 mm in length and is secured to distal end 308 of catheter shaft 304 by methods known in the art, including gluing, melting or welding.

Guidewire 302 includes a proximal end 316 and a distal end 314. Guidewire 302 passes through a centrally-located guidewire lumen of catheter shaft 304 and extends through balloon 312 of balloon catheter 300. Distal end 314 is more flexible than proximal end 316 for greater maneuverability. The flexibility of distal end 314 may be achieved by tapering guidewire 302 to a reduced diameter at distal end 314, or by constructing distal end 314 from a more flexible material than proximal end 316. Optionally, guidewire 302 may include a spring at distal end 314 that reduces its stiffness relative to proximal end 316. In one embodiment, guidewire 302 is rounded at a tip of distal end 314. In one embodiment guidewire 302 is a steerable guidewire, as is known in the art, that can be easily manipulated through a tortuous blood vessel.

Distal end 314 of guidewire 302 is bent to one side at a bend 318, as shown in FIG. 3. Bend 318 aids in manipulation and insertion of guidewire 302 through the blood vessel by simplifying the ability to track the guidewire along the proper course at branching vessels. While advancing guidewire 302 to the treatment site, the guidewire itself may be rotated by manipulating proximal end 316. Rotation is readily accomplished byway of guidewire manipulator 320. In one embodiment, guidewire manipulator 320 is a knurled handle which fits over proximal end 316 of guidewire 302 and can be rotated between a physician's thumb and index finger to apply torsion loads, and pushed and pulled to apply axial loads.

In use, guidewire 302 is introduced into a blood vessel through an incision and tracked through the blood vessel, uses radiopaque markers as well as known in the art, to a location just past the target site. Balloon catheter 300, which includes the centrally-located guidewire lumen, is back-loaded onto guidewire 302 and guided through the blood vessel over guidewire 302 until properly positioned, with balloon 312 located within the region of stenosis. Guidewire 302 may then be removed by withdrawing it out of the proximal end of balloon catheter 300 through luer hub 310. Balloon catheter 300 is thereby positioned within the blood vessel for use to treat the stenosis. Optionally, the angioplasty procedure may be performed without removing the guidewire from the guidewire lumen of the balloon catheter.

Figure 4:
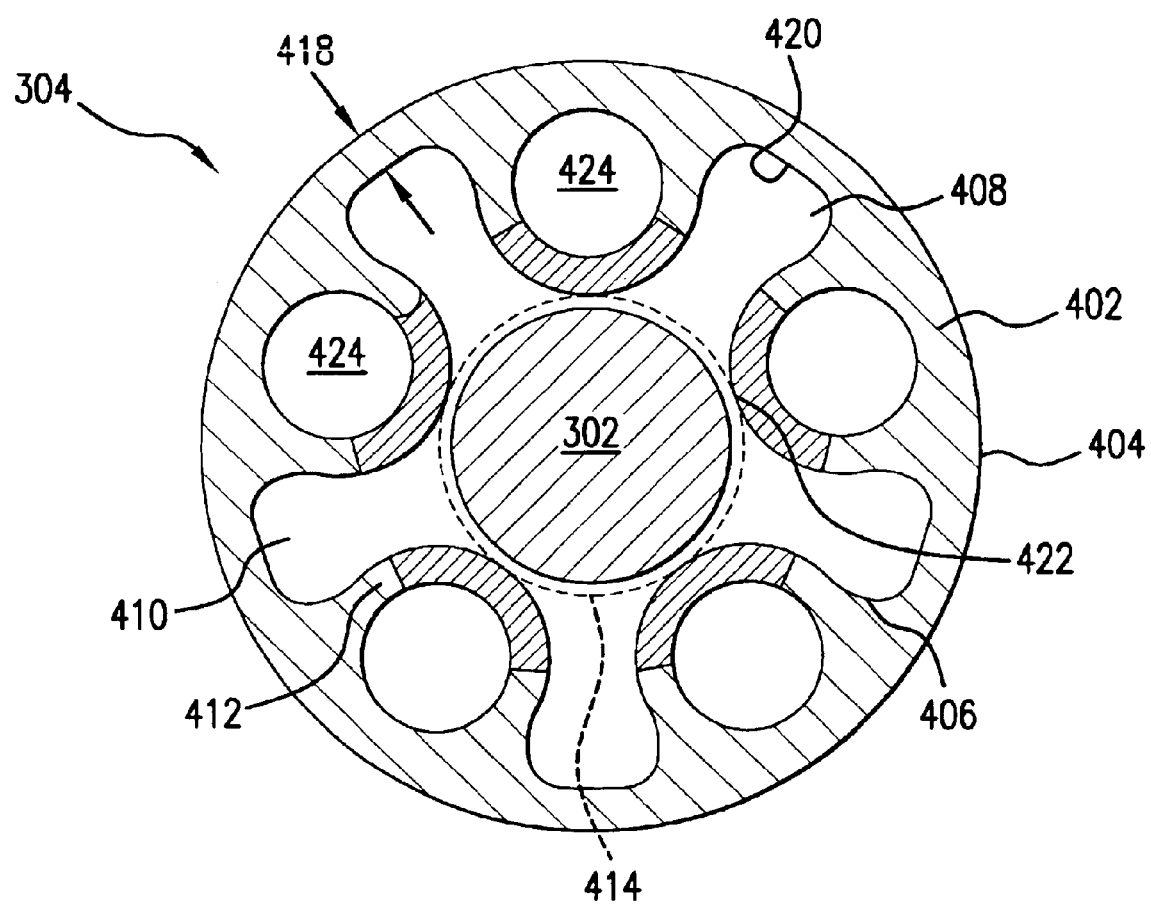
FIG. 4 is a cross-sectional view of an embodiment of the present invention taken along line A—A of FIG. 3.

FIG. 4 shows a cross-sectional view of an embodiment of catheter shaft 304 taken along line A—A in FIG. 3. As shown in FIG. 4, catheter shaft 304 includes a body portion 402. Body portion 402 is formed from a solid, yet flexible material, such as nylon. Nylon is a flexible material which imparts a balloon catheter constructed therefrom with a high impact strength and a high burst strength. Such a catheter constructed from nylon is also fit for use in a wide range of temperatures, exhibits good chemical resistance and good bio-compatibility. However, body portion 402 may be constructed from any other material suitable for a catheter body, such as polymeric materials including: silicone rubber, polypropylene, polyethylene, polyvinylchloride, fluoropolymers and the like, as would be apparent to one skilled in the relevant art.

Body portion 402 is flexible along its length, and has a substantially fixed outer diameter so that the size of the catheter body is substantially consistent along its length. In an alternate embodiment, catheter body portion is tapered along its length, or optionally, only along a distal region thereof, to impart increased flexibility to the distal end. In another embodiment, distal end 308 of catheter body portion 402 is comprised of a more flexible material than proximal end 306 of catheter body portion 402.

Body portion 402 comprises an exterior wall surface 404 and an interior wall surface 406. In the embodiment shown in FIG. 4, exterior wall surface 404 has a substantially circular cross-section with a fixed outer diameter. In one embodiment exterior wall surface 404 of body portion 402 has an outer diameter between 0.030 and 0.080 inch, and in another embodiment between 0.030 and 0.056 inch. However, as stated above, the outer diameter at different locations along balloon catheter 300 may vary if catheter shaft 304 is tapered along its length.

Interior wall surface 406 of catheter shaft 304 forms a non-circular central guidewire lumen 408. In the embodiment shown in FIG. 4, guidewire lumen 408, formed by interior wall surface 406, is substantially star-shaped, having a plurality of guidewire lumen arms 410 extending between nodes 412. Nodes 412 are part of body portion 402 and extend between and define guidewire lumen arms 410. Together, nodes 412 and arms 410 form a guidewire track 414 in guidewire lumen 408. Guidewire track 414 is a theoretical circular perimeter (shown in dashed lines) intersecting an innermost point of each node 412. The diameter of guidewire track 414 is a maximum diameter that a guidewire for use in the balloon catheter of the present invention can be and still fit within the guidewire lumen.

Guidewire lumen arms 410 extend from guidewire track 414 of guidewire lumen 408 toward exterior wall surface 404 to form a location of minimum wall thickness between exterior wall surface 404 and interior wall surface 406, as is shown at reference numeral 418. In one embodiment, minimum wall thickness 418 is within the range of 0.0005 inch to 0.0080 inch, and in another embodiment, minimum wall thickness 418 is within the range of 0.0015 inch to 0.0060 inch. However, minimum wall thickness 418 may vary depending on the desired outer diameter of body portion 402, the length of arms 410, and the desired diameter of guidewire track 414. Minimum wall thickness 418 enables body portion 402 to be flexible, aiding in the insertion of catheter 304 through a patient's tortuous blood vessels.

In one embodiment, guidewire lumen arms 410 include a basal surface 420 that lies generally concentric with exterior wall surface 404. Basal surface 420 provides a relief between adjacent nodes for stress that would be incurred if arms 410 formed points, or, in other words, if adjacent nodes came together to form a point. Although basal surface 420 is shown substantially concentric with exterior wall 404, basal surface need not be concentric with exterior wall 404, but may be non-concentric, may be planar, or may have an arc-shape or any other shape that would form a stress relief, as would be apparent to one skilled in the relevant art. Additionally, arms 410 may have a consistent width, or may taper in either a direction away from guidewire track 414 or in a direction toward guidewire track 414. Finally, arms 410 need not extend "deep" between nodes 412, but may be indentations or curves that separate nodes 412, thereby increasing the minimum wall thickness shown at 418.

Nodes 412 are arc-shaped extensions of body portion 402 that extend into and narrow guidewire lumen 408. Nodes 412 are separated from each other by guidewire lumen arms 410. Nodes 412 are convex-arcs, each of which has an innermost point that forms a portion of guidewire track 414 such that guidewire 302 slides thereon.

In the embodiment of FIG. 4, each node includes an innermost region comprising a crown 422. Crown 422 includes the innermost point of node 412, which intersects with, and thereby forms a portion of, guidewire track 414. Crown 422 extends outward from the point of intersection with guidewire track 414, toward exterior wall surface 404. The distance that crown 422 extends is not a critical factor of the invention of this embodiment, but crown 422 includes the point of intersection of node 412 with guidewire track 414. In this embodiment, crown 422 is formed of a material different than the material of the rest of body portion 402, as is denoted by the cross-hatching in FIG. 4. Accordingly, in this embodiment, catheter 304 is formed of at least two materials.

In the embodiment shown in FIG. 4, the material of crown 422 forms all of crown 422. As such, only node 412 is formed of two materials. However, as would be apparent to one skilled in the relevant art, all of node 412 could be formed of one material and the remaining material of body portion 402 could be formed of a second material.

In one embodiment, crown 422 is formed of a material having a lower coefficient of friction than the material forming the rest of body portion 402. One material meeting this criteria is HDPE, viz., high density polyethylene. However, any other material having a similar or lower coefficient could be used. Other materials, such as TEFLON, polypropylene and polyethylene could be used to form crown 422 as would be apparent to one skilled in the relevant art.

Guidewire 302 is disposed within guidewire lumen 408. In one embodiment, guidewire 302 has a diameter that is slightly smaller than the diameter of guidewire track 414 to minimize the friction and contact between crown 422 of node 412 and guidewire 302. In a preferred embodiment, each crown 422 contacts guidewire 302 at only a single point in cross-section.

During use, crown 422 of each node 412 engages guidewire 302 as the catheter is advanced there over, providing low-friction contact between guidewire 302 and dilatation catheter 300. The material of crown 422, having a low coefficient of friction allows the catheter of the present invention to be advanced around sharper bends with substantially less axial force than is required to advance standard catheters due to "rolling" rather that "sliding" friction between the catheter of the present invention and the guidewire.

In the embodiment of FIG. 4, each node 412 includes an inflation lumen 424 formed therein. Each inflation lumen 424 extends from proximal end 306 of catheter shaft 304 to inflatable balloon 312 attached to distal end 308 of catheter shaft 304.

Inflation lumens 424 are in fluid communication with the inflatable balloon of the balloon catheter, and are used to inflate and deflate the balloon. After the balloon catheter is properly positioned in a blood vessel, an inflation fluid is forced through at least one inflation lumen 424 to inflate the balloon, forcing the balloon to expand against the interior of the blood vessel. After expansion, the balloon is deflated either through the same inflation lumen used for inflation.

Inflation lumens 424 are isolated from each other and from guidewire lumen 408, such that they do not fluidly communicate with each other within catheter shaft 304. Inflation lumens 424 extend substantially parallel to guidewire lumen 408, substantially the length of catheter shaft 304. Furthermore, inflation lumens 424 are constructed to be structurally sound, in that the inflation lumens maintain their original diameter even when under pressure. As such, the outer diameter or the circumference of catheter shaft 304 does not vary when inflation lumens 424 are pressurized.

In other embodiments, the catheter shaft of the present invention includes three, four, five, six, seven or a greater number of nodes and guidewire lumen arms. Additionally, each node need not include an inflation lumen extending there through.

In one embodiment, the dilatation catheter of the present invention includes seven nodes with only one inflation lumen extending through one of the nodes. The remaining six nodes do not include an inflation lumen, and may be solid or configured for another purpose, such as introduction of one or more dyes, drugs, electrical wiring, multiple balloons or diagnostic devices to a distal end of the catheter.

Figure 5:
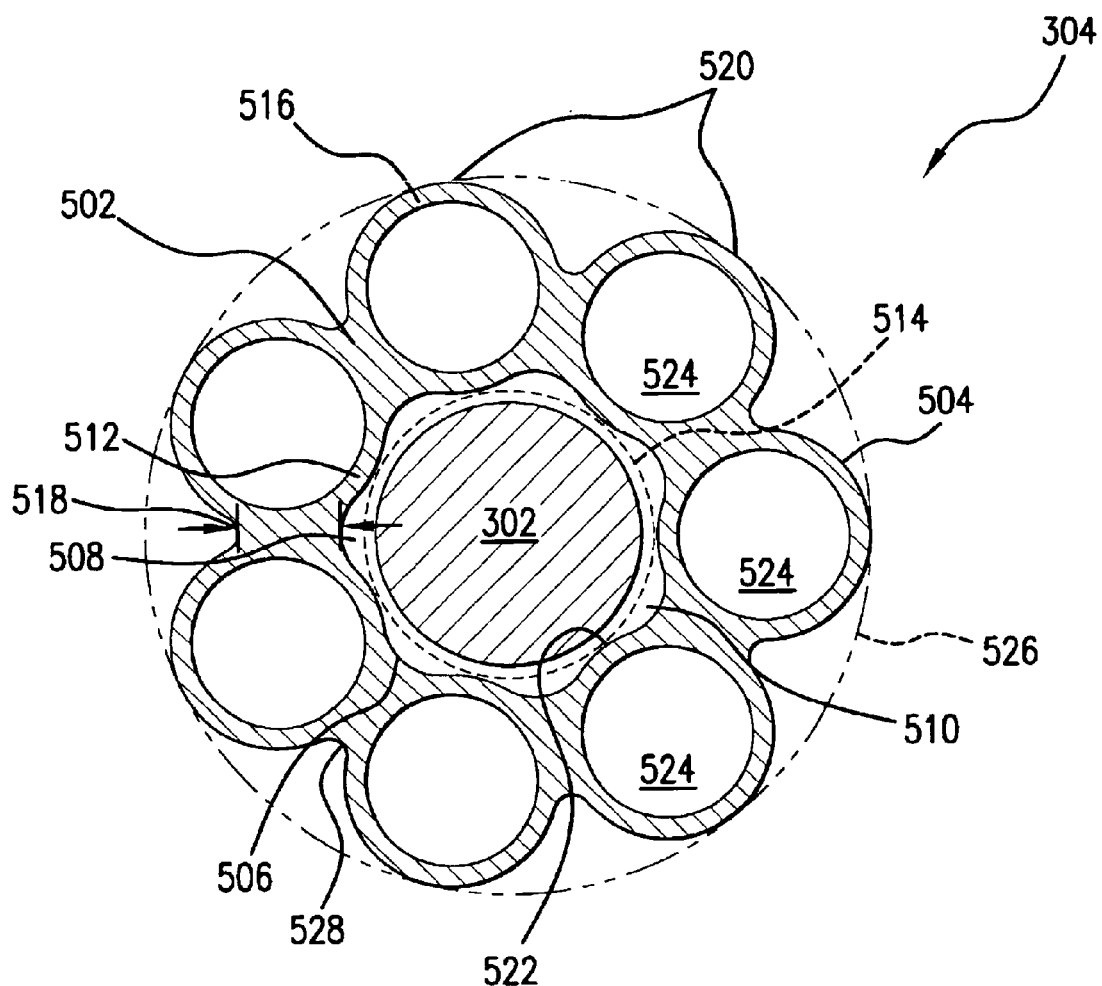
FIG. 5 is a cross-sectional view of another embodiment of the present invention taken along line A—A of FIG. 3.

Another embodiment of catheter shaft 304 of the present invention is shown in FIG. 5. FIG. 5 shows a cross-sectional view of catheter shaft 304 taken along line A—A of FIG. 3. This embodiment of catheter shaft 304 has an exterior wall surface 504 and an interior wall surface 506 forming a centrally located non-circular guidewire lumen 508. Catheter shaft 304 may be formed of the same materials and may include the same physical characteristics and properties as the embodiment described with reference to FIG. 4.

Interior wall surface 506 includes nodes 512 and guidewire lumen arms 510, that form guidewire lumen 508. In this embodiment, catheter shaft 304 includes seven nodes 512 and seven guidewire lumen arms 510, creating a peak-and-valley cross-section. Nodes 512 are arc-shaped, convex walls that extend into and narrow guidewire lumen 508.

Nodes 512 are convex-arcs that each have an innermost point that intersects with and defines a theoretical guidewire track 514 (shown in dashed line). Arms 510 of guidewire lumen 508 extend from guidewire track 514 of guidewire lumen 508 toward exterior wall surface 504 to form a location of minimum thickness 518 between exterior wall surface 504 and guidewire lumen 508.

In one embodiment, arms 510 include a smooth concave surface that lies generally between each convex-shaped node 512. The smooth concave surface eliminates stress risers, which reduces the chance of separation of one node from another and reduces the incidence of crack propagation during manufacturing. However, arms 510 need not be convex-shaped arcs, but could be angled, tapered or otherwise curved, as would be apparent to one skilled in the relevant art.

As described above with reference to FIG. 4, each node includes a region comprising a crown 522. Crown 522 includes the innermost point of node 512, which intersects with guidewire track 514. Crown 522 extends outward from the point of intersection with guidewire track 514, toward exterior wall surface 504. As described above with reference to FIG. 4, crown 522 may be formed of a material different than the material of the rest of catheter shaft 304 (not shown). Accordingly, catheter shaft 304 could be formed of at least two materials.

When formed of two materials, the material in the region of crown 522 may be used to form only crown 522, or the entire node 512. As such, all of node 512 may be formed of one material and the remaining material of catheter shaft body portion 502 could be formed of a second material, or node 512 could be formed of two or more materials.

In one embodiment when catheter shaft 304 is formed of two materials, crown 522 is formed of a material having a lower coefficient of friction than the material forming the rest of catheter shaft 304, such as is described above with reference to the embodiment shown in FIG. 4.

FIG. 5 also shows guidewire 302 in guidewire lumen 508. The guidewire has a diameter slightly less than the diameter of guidewire track 514. In a preferred embodiment, crown 522 of each node 512 contacts guidewire 302 at only a single point in cross-section. Crown 522 of each node 512 engages guidewire 302 as dilatation catheter 300 is advanced over the guidewire, to provide a low-friction contact between the guidewire and the dilatation catheter. The material of crown 522, having a low coefficient of friction, allows the catheter to be advanced over sharper bends with substantially less axial force than is required to advance standard catheters. Furthermore, nodes 512 form bumps that enable the guidewire to roll over the nodes as the catheter is advanced over the guidewire. This results in much less friction than sliding the guidewire in a smooth inner lumen.

In the embodiment of FIG. 5, each node 512 includes an inflation lumen 524. Each inflation lumen 524 extends from proximal end 306 of catheter shaft 304 to inflatable balloon 312 attached to distal end 308 thereof.

At least one of inflation lumens 524 is in fluid communication with inflatable balloon 312 of the balloon catheter of the present invention, and is used to inflate/deflate the balloon. Inflation lumens 524 are isolated from each other and from guidewire lumen 508 within catheter shaft 304. Inflation lumens 524 extend substantially parallel to guidewire lumen 508, substantially the length of catheter shaft 304. Furthermore, the inflation lumens are constructed to be structurally sound, in that the inflation lumens maintain their original diameter even when under pressure. As such, the outer diameter or the circumference of the catheter shaft does not vary when inflation lumens 524 are pressurized.

In this embodiment, exterior wall surface 504 of catheter shaft 304 includes exterior nodes 516. Exterior nodes 516 are convex-shaped arcs that extend from body portion 502. As shown in FIG. 5, exterior nodes 516 are merely the exterior walls of each inflation lumen 524. As such, the convex shape of exterior nodes 516 is concentric with the inflation lumen. However, as would be apparent to one skilled in the relevant art, the shape of exterior nodes 516 need not be concentric with inflation lumens 524.

As stated above, the exterior nodes are the exterior walls of each inflation lumen 524. In one embodiment, the exterior wall of each inflation lumen has a thickness in the range of 0.0005 to 0.0080 inch, in another embodiment the thickness is in the range of 0.0015 to 0.0060 inch. The interior wall between inflation lumen 524 and node 512 may have the same thickness, or maybe thicker or thinner depending on the material used to form the catheter shaft, as would be apparent to one skilled in the relevant art.

The outermost point 520 of each exterior node 516 forms a theoretical circular perimeter 526 of dilatation catheter 300, as is denoted by the dashed line in FIG. 5.

Exterior wall surface 504 includes regions between each exterior node 516 that form indentations 528. Indentations 528 are formed by the curves of exterior nodes 516 and extend toward the interior of dilatation catheter 300 within outer diameter 526. In one embodiment, the deepest point of each indentation 528 is an arc formed between, and connecting two exterior nodes 516 disposed on either end of each indentation 528. The arc eliminates stress risers, which reduces the chance of stress fractures and crack propagation that may result in the separation of one node from another. However, in further embodiments it may be advantageous to form the indentations to a point, or to be squared-off, or otherwise shaped, as would be apparent to one skilled in the relevant art.

Indentations 528 allow catheter shaft 304 of balloon catheter 300 to be more flexible and enable easier tracking over a guidewire in a tortuous blood vessel. Additionally, when balloon catheter 300 is introduced into a patient's blood vessel through a guide catheter, indentations 528 provide additional "open area" between the guide catheter and exterior wall surface 504 thereby easing insertion and travel of the catheter therethrough. An increase in the open area also allows increased flow rates of dye injection or other injection through the lumen of the guide catheter for diagnostic purposes.

In other embodiments, dilatation catheter 300 includes between three and eight, or a greater number of nodes and arms. Additionally, as described with reference to FIG. 4, each node need not include an inflation lumen extending therethrough. In one embodiment, the catheter includes seven nodes and only one inflation lumen extending through one of the nodes. The other six nodes include no inflation lumen, but are solid nodes. As stated above with reference to FIG. 4, the catheter of the present invention includes an odd number of nodes that form the guidewire track. Nevertheless, the catheter of the present invention could have an odd or an even number of nodes. Dilatation catheter 300 is compatible with guide catheters smaller than 6 French, but maybe used with larger catheters, as would be apparent to one skilled in the relevant art.

Catheter shaft 304 of the present invention is attached to balloon 312 such that the inflation lumens thereof are in fluid communication with the interior of the balloon. Accordingly, the balloon is inflated or deflated through the inflation lumens. Attachment of balloon 312 to catheter shaft 304 is shown and described with reference to FIG. 6.

Figure 6:
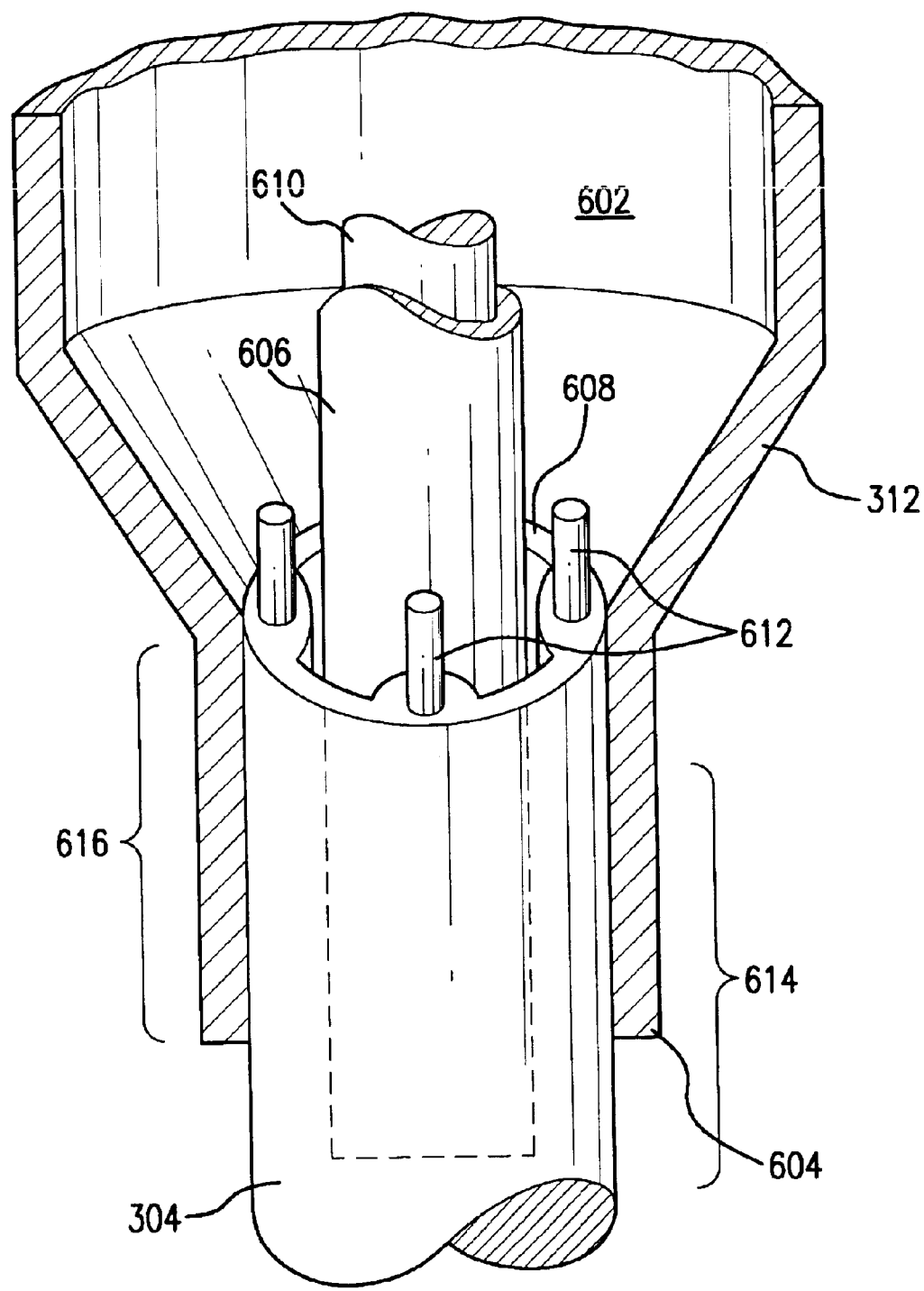
FIG. 6 is a perspective view of a portion 600 of the balloon catheter of FIG. 3, including mandrels used to form the bond between a catheter shaft made according to the present invention and the balloon.

A portion of distal end 308 of catheter shaft 304 and balloon 312, are shown in FIG. 6. In order to better view the attachment of balloon 312 to distal end 308 of catheter shaft 304, balloon 312 is shown in cross-section. Catheter shaft 304 is the catheter shaft shown and described above with reference to FIG. 4, except that catheter shaft 304 has only four nodes. However, as would be apparent to one skilled in the relevant art, the catheter shaft of FIG. 5 could also be assembled using the same method and technique.

Balloon 312 includes a proximal end 604 and distal end (not shown). Balloon 312 forms an interior chamber 602 which is in fluid communication with the inflation lumens of catheter shaft 304. Catheter 300 includes an inner member 606. Inner member 606 extends into distal end 308 of catheter shaft 304, as shown by the dashed lines. Inner member 606 extends from distal end 308 of catheter shaft 304, through balloon 312, and out the distal end of the balloon. As will be explained below, the distal end of the balloon is sealed about a distal end of inner member 606, sealingly closing balloon 312. Inner member 606 forms a guidewire lumen that extends through balloon 312 and out a distal end thereof (not shown).

Inner member 606 is a tube and is formed of either the same or different material as catheter shaft 304. Inner member should be comprised of a material that is easily bonded to catheter shaft 304. A guidewire mandrel 610 is shown disposed in an interior lumen of inner member 606. Additional inflation lumen mandrels 612 are disposed in the inflation lumens of catheter shaft 304.

During manufacturing, guidewire mandrel 610 is inserted into inner member 606. Inner member 606, along with guidewire mandrel 610, are inserted into the guidewire lumen of catheter shaft 304. Also, inflation lumen mandrels are inserted into the inflation lumens of catheter shaft 304. One end of balloon 312 is disposed about the exterior of catheter shaft 304. A laser welding unit melts an exterior surface of inner member 606 to an interior surface of catheter shaft 304 along a catheter bond zone 614. Also, the laser welding unit melts balloon 312 to an exterior surface of catheter shaft 304 at a balloon bond zone 616.

During the welding process, the inflation lumen mandrels 612 and the guidewire mandrel 610 maintain the lumens so that they do not become occluded by the melting materials. After the welding process is complete, the inflation lumen mandrels 612 are withdrawn, leaving open passages. Accordingly, the inflation lumens are then in open fluid communication with interior chamber 602 of balloon 312.

After inflation mandrels 612 are removed from catheter shaft 304, the distal end of balloon 312 is welded to the distal end of inner member 606, sealing and enclosing balloon chamber 602. During this welding process, guidewire mandrel 610 is still contained within inner member 606. As explained above, this eliminates any occlusion or diametric change of the guidewire lumen. At completion of the welding process at the distal end of balloon 312 and the distal end of inner member 606, guidewire mandrel 610 is withdrawn through the distal end of inner member 606, and an open guidewire lumen extends from catheter shaft 304, through inner member 606 to the distal end of balloon 312.

Other methods may be used to bond balloon 312 and inner member 606 to catheter shaft 304. For instance, an adhesive or a cement could be used alone or in combination with the earlier described heat or laser means, as would be apparent to one skilled in the art.

Figure 8:
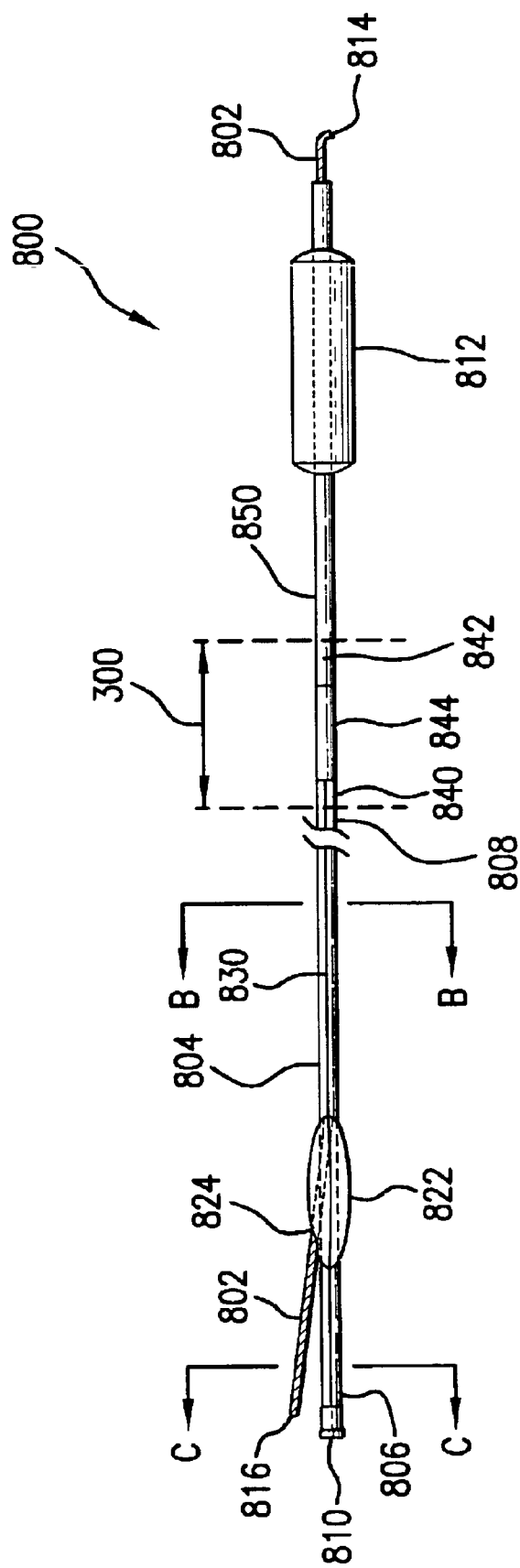
FIG. 8 is a view of an MX balloon catheter and guidewire assembly according to the present invention.

Referring now to FIG. 8, another embodiment of a dilatation or balloon catheter 800 is shown. Dilatation catheter 800 is shown in FIG. 8 as tracked on a guide wire 802 having a proximal end 816 and a distal end 814. Dilatation catheter 800 includes a proximal region 840, a distal region 842 and a bond region 844. Proximal region 840 includes a proximal catheter shaft 804 having a proximal end 806 and a distal end 808. Distal region 842 and bond region 844 are discussed in detail below with respect to FIG. 13.

Dilatation catheter 800 is similar to the dilatation catheter of FIG. 3 and includes a hub 810 and a dilatation balloon 812. However, where the dilatation catheter of FIG. 3 is an OTW catheter design, dilatation catheter 800 is an easily exchangeable MX catheter design. In an MX catheter of the type shown in FIG. 8, guidewire 802 has a guide member 822 which slides along proximal catheter shaft 804. As it moves along proximal catheter shaft 804, guide member 822 opens a cut 830 that runs the length of proximal catheter shaft 804 and guides guidewire 802 out of proximal catheter shaft 804. Thus, the portion of guidewire 802 that is distal to guide member 822 is disposed within proximal catheter shaft 804 and the portion of guidewire 802 that is proximal guide member 822 is disposed outside of proximal catheter shaft 804.

The MX guide member 822 acts as a moveable proximal guidewire exit and is slidably positionable along the cut 830, such that proximal end 816 of guidewire 802 will go through proximal guidewire exit 824 of guide member 822. Thus, a user can control guidewire 802 from a location distal to proximal end 806 of dilatation catheter 800.

Holding and/or securing guide member 822 and guidewire 802, dilatation catheter 800 is advanced into the vasculature over guidewire 802. While dilatation catheter 800 is being advanced, guidewire 802 is enveloped within a guidewire lumen. Additionally, guide member 822 can be slidably advance proximally along proximal catheter shaft 804 as dilatation catheter 800 is advanced into the vasculature, enclosing guidewire 802 that is proximal to guide member 822.

If at any point during the procedure, dilatation catheter 800 needs to be exchanged, this can be achieved by simply pulling the dilatation catheter 800 out of the vasculature while holding and sliding guide member 822 distally along the cut 830 toward distal end 808 of proximal catheter shaft 804. As dilatation catheter 800 is pulled out, control of guidewire 802 will switch from a point just proximal to distal end 808 of proximal catheter shaft 804 to a point distal of dilatation balloon 812. Therefore, dilatation catheter 800 can be removed entirely from guidewire 802 without the user losing control or position thereof, such that another device may be slid onto indwelling guidewire 802.

If on the other hand, guidewire 802 needs to be exchanged, it simply requires pulling guidewire 802 proximally through proximal guidewire exit 824 while holding the catheter in position. A new guidewire may be forward loaded into proximal guidewire exit 824, tracked through proximal catheter shaft 804, and positioned at the treatment site.

Figure 9:
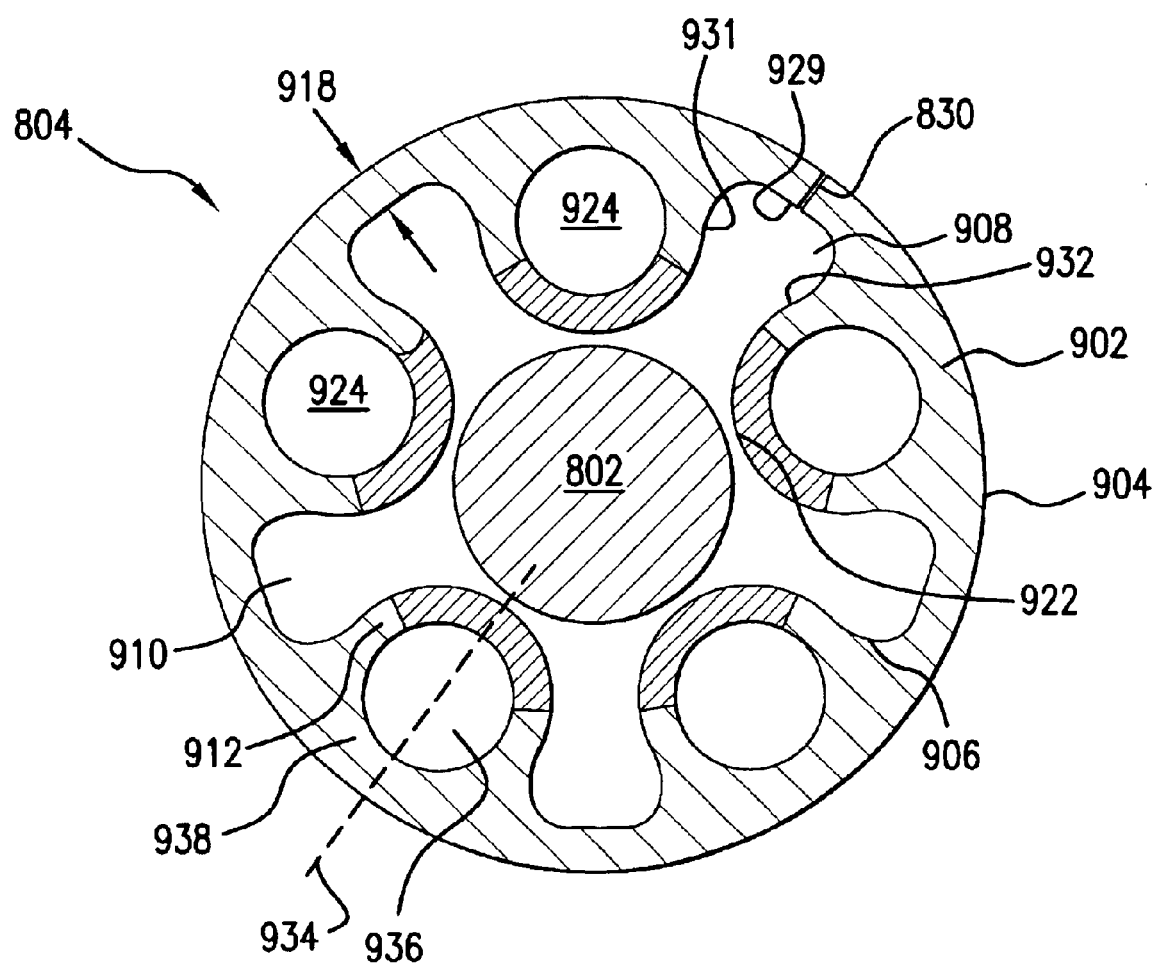
FIG. 9 is a cross-sectional view of an embodiment of the present invention taken along line B—B of FIG. 8.

FIG. 9 shows a cross-sectional view of an embodiment of proximal catheter shaft 804 taken along line B—B in FIG. 8. As shown in FIG. 9, proximal catheter shaft 804 includes a body portion 902. Body portion 902 is substantially similar to body portion 402 of FIG. 4. Body portion 902 comprises an exterior wall surface 904 and an interior wall surface 906. Interior wall surface 906 of proximal catheter shaft 804 forms a non-circular central guidewire lumen 908. Proximal catheter shaft 804 may be formed of the same materials and may include the same physical characteristics, properties, and advantages as the embodiment described with reference to FIG. 4. Further, any variations discussed above that would be appropriate for the embodiment described with respect to FIG. 4 would likewise be suitable for the embodiment described with respect to FIG. 9.

In the embodiment shown in FIG. 9, guidewire lumen 908, formed by interior wall surface 906, is substantially star-shaped, having a plurality of guidewire lumen arms 910 extending between nodes 912. Nodes 912 are part of body portion 902 and extend between and define guidewire lumen arms 910. FIG. 9 also shows guidewire 802 in guidewire lumen 908. Guidewire 802 slides over crown regions 922 of nodes 912 as discussed above with respect to FIG. 4. One or more nodes 912 may include an inflation lumen 924 formed therein. Each inflation lumen 924 extends from proximal end 806 of proximal catheter shaft 804 to distal end 808 of proximal catheter shaft 804. The operation of inflation lumens is the same as discussed above with respect to FIG. 4. Guidewire lumen arms 910 extend toward exterior wall surface 904 to form a location of minimum wall thickness between exterior wall surface 904 and interior wall surface 906, as is shown at reference numeral 918.

A cut 830 extends between exterior wall surface 904 and interior wall surface 906. Guide member 822 opens guidewire lumen 908 at cut 830 and provides an exit for guidewire 802, such that guidewire 802 is removed from guidewire lumen 908 when tracked through guide member 822. Preferably, cut 830 is located at an apex 929 of one of guidewire lumen arms 910 where wall thickness 918 is minimal. Thus, as guide member 822 opens cut 830, walls 931 and 932 of guidewire lumen arm 910 move apart from each other forming a large gap between adjacent nodes 912. Guide member 822 can work in several ways. However, guide member 822 generally pushes apart walls 931 and 932 of adjacent guidewire lumen arms 910 having the cut therein and separates them at least far enough that guidewire 802 can be tracked through cut 830 to escape proximal catheter shaft 804.

Alternatively, cut 830 may occur at any other location of body portion 902, provided that it extends from interior surface 906 to exterior surface 904. For example, cut 830 can be disposed on a line 934 across a center section 936 of node 912 that is not being used as an inflation lumen 924. In this embodiment, guide member 822 would cause center section 936 to split and separate, such that guidewire 802 can be removed from proximal catheter shaft 804. A cut along line 934 extends through two parts of body portion 902 (viz., crown portion 922 and a region 938 between center section 936 and exterior wall surface 904).

Figure 10:
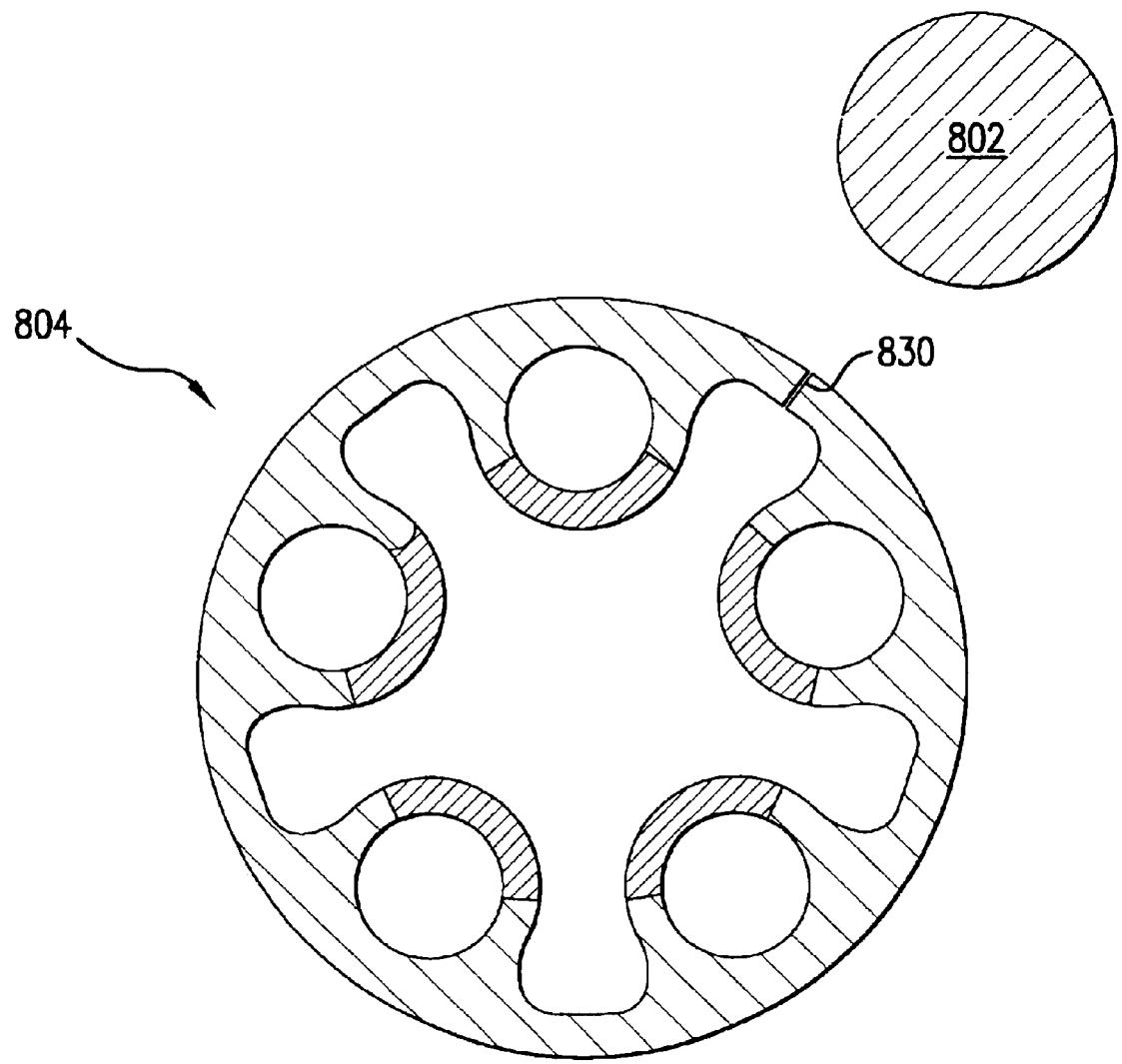
FIG. 10 is a cross-sectional view of the embodiment of FIG. 9 taken along line C—C of FIG. 8.

FIG. 10 is a cross-sectional view of the embodiment of FIG. 9 taken along the line C—C of FIG. 8. In a natural state, cut 830 is tightly closed, such that proximal catheter shaft 804 operates the same as catheter shaft 304 of FIG. 4, which does not have cut 830. Thus, guide member 822 must force open cut 830 to allow guidewire 802 to escape. As guide member 822 moves away from a particular position along proximal catheter shaft 804, cut 830 closes again behind guide member 822 with guidewire 802 exiting out of guide member 822.

Figure 11:
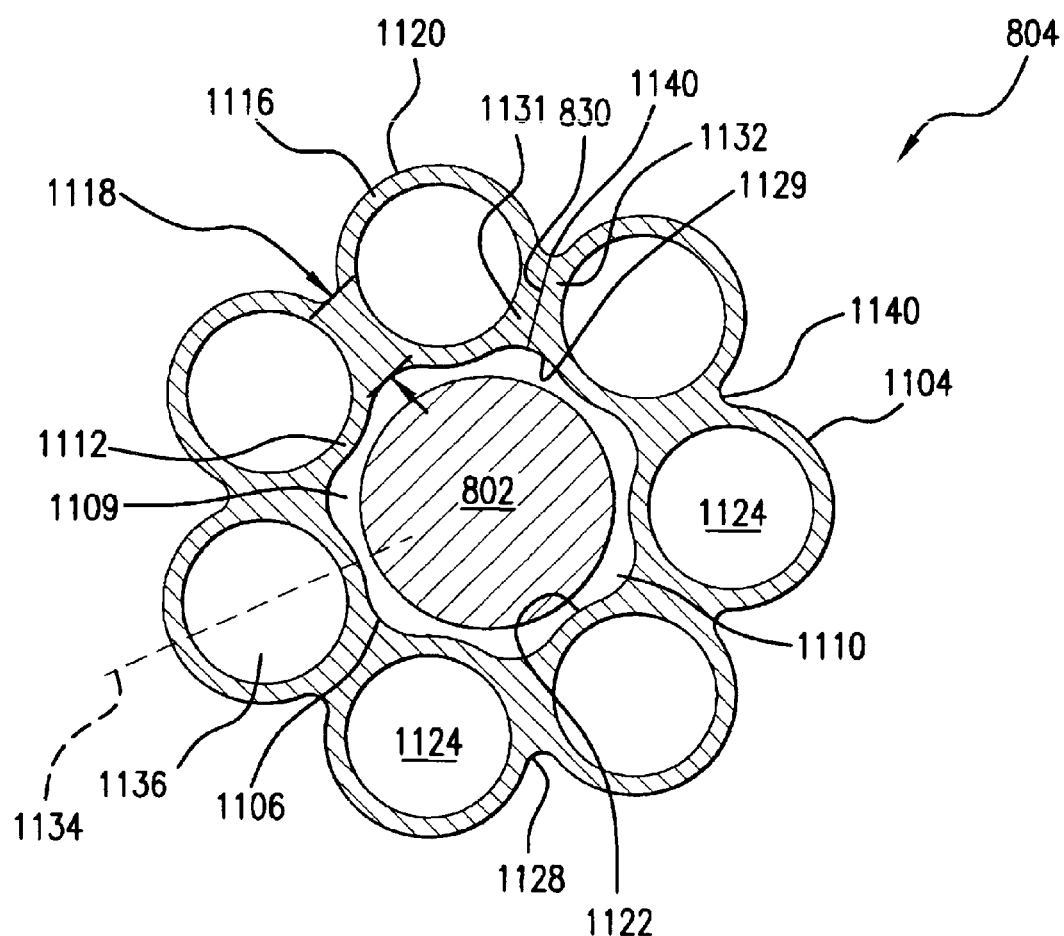
FIG. 11 is a cross-sectional view of another embodiment of the present invention taken along line B—B of FIG. 8.

Another embodiment of proximal catheter shaft 804 of the present invention is shown in FIG. 11. FIG. 11 shows a cross-sectional view of proximal catheter shaft 804 taken along line B—B of FIG. 8. This embodiment of proximal catheter shaft 804 is similar to the embodiment described above for FIG. 5 in that is has an exterior wall surface 1104 and an interior wall surface 1106 forming a centrally located non-circular guidewire lumen 1108. The embodiment described in FIG. 11 has the same materials and may include the same physical characteristics, properties, and advantages as the embodiment described with reference to FIG. 5. Further, any variations discussed above that would be appropriate for the embodiment described with respect to FIG. 5 would likewise be suitable for the embodiment described with respect to FIG. 11.

Interior wall surface 1106 includes nodes 1112 and guidewire lumen arms 1110, that form guidewire lumen 1108. In this embodiment, arms 1110 of guidewire lumen 1108 extend toward exterior wall surface 1104 to form a location of minimum thickness 1118 between exterior wall surface 1104 and guidewire lumen 1108.

In one embodiment, arms 1110 include a smooth concave surface that lies generally between each convex-shaped node 1112. FIG. 11 also shows guidewire 802 in guidewire lumen 1108. Guidewire 802 slides over nodes 1112 as discussed above with respect to FIG. 5. In the embodiment of FIG. 11, one or more nodes 1112 includes an inflation lumen 1124. Each inflation lumen 1124 extends from proximal end 806 of proximal catheter shaft 804 to distal end 808 thereof. The operation of inflation lumens 1124 is the same as discussed above with respect to FIG. 5.

In this embodiment, exterior wall surface 1104 of proximal catheter shaft 804 includes exterior nodes 1116 and regions between each exterior node 1116 that form indentations 1128, the advantages, operation and suitable variations of which are discussed in detail above with respect to FIG. 5.

In the embodiment of FIG. 11, a cut 830 extends between exterior wall surface 1104 and interior wall surface 1106. Guide member 822 opens guidewire lumen 1108 at cut 830 such that guidewire 802 can be removed from guidewire lumen 1108, as described above with respect to FIG. 9. Preferably, cut 830 is located between at an apex 1129 of guidewire lumen arms 1110 and a lowest point 1140 of indentation 1128 where the wall thickness 1118 is minimal. Thus, as guide member 822 opens cut 830, adjacent walls 1131 and 1132 are created by cut 830. Walls 1131 and 1132 move apart from each other forming a large gap therebetween. Walls 1131 and 1132 separate at least far enough that guidewire 802 can pass through cut 830 to escape proximal catheter shaft 804.

Similar to the embodiment of FIG. 9, cut 830 may occur at any other location of proximal catheter shaft 804, provided that it extends from the interior wall surface 1106 to the exterior wall surface 1104. For example, cut 830 can be disposed on a line 1134 across a center section 1136 that is not being used as an inflation lumen 1124. In this embodiment, guide member 822 would cause center section 1136 to open and separate, such that guidewire 802 can be removed from proximal catheter shaft 804. Cut 830 extends through crown portion 1122 and an exterior node 1116 between the interior wall surface 1106 and exterior wall surface 1104.

Figure 12:
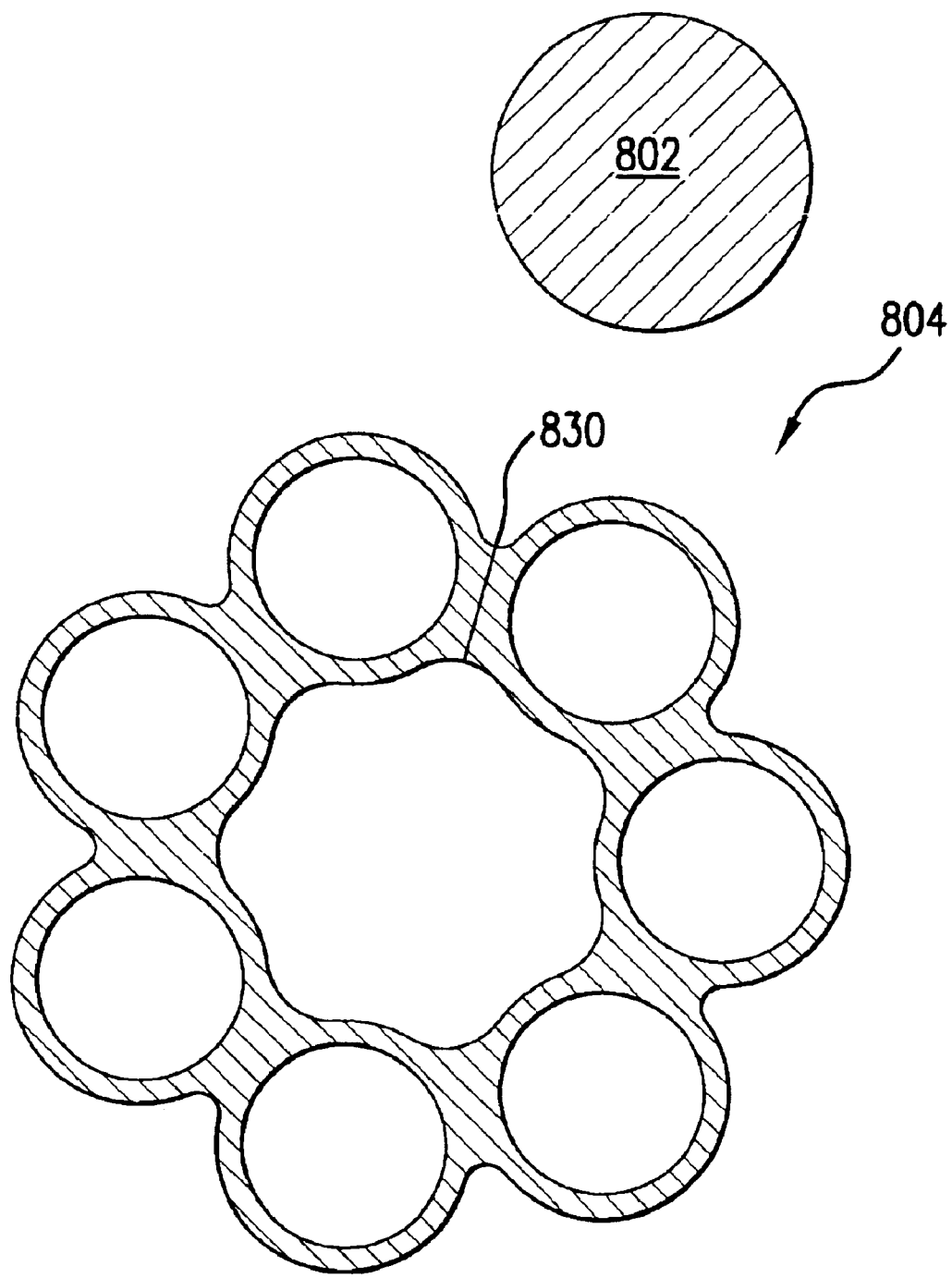
FIG. 12 is a cross-sectional view of the embodiment of FIG. 11 taken along line C—C of FIG. 8.

FIG. 12 is a cross-sectional view of the embodiment of FIG. 11 taken along the line C—C of FIG. 8, in which cut 830 is closed after guide member 822 has allowed guidewire 802 to escape as discussed above with respect to FIG. 10.

Referring again to FIG. 8, dilatation catheter 800 includes proximal region 840, distal region 842 and bond region 844. Proximal region 840 is bonded to distal region 842 in the bond region 844. While proximal region 840 generally comprises one of catheter shaft 304 or 804, distal region 842 is generally a coaxial shaft segment. Distal region 842 includes a distal catheter shaft 850 and a distal guidewire shaft 1306 (see FIG. 13) running coaxially within distal catheter shaft 850. Thus, the very distal portion of the dilatation catheter 800 has the advantatge of having increased flexibility for traversing the particularly tortuous areas of the vasculature.

Figure 13:
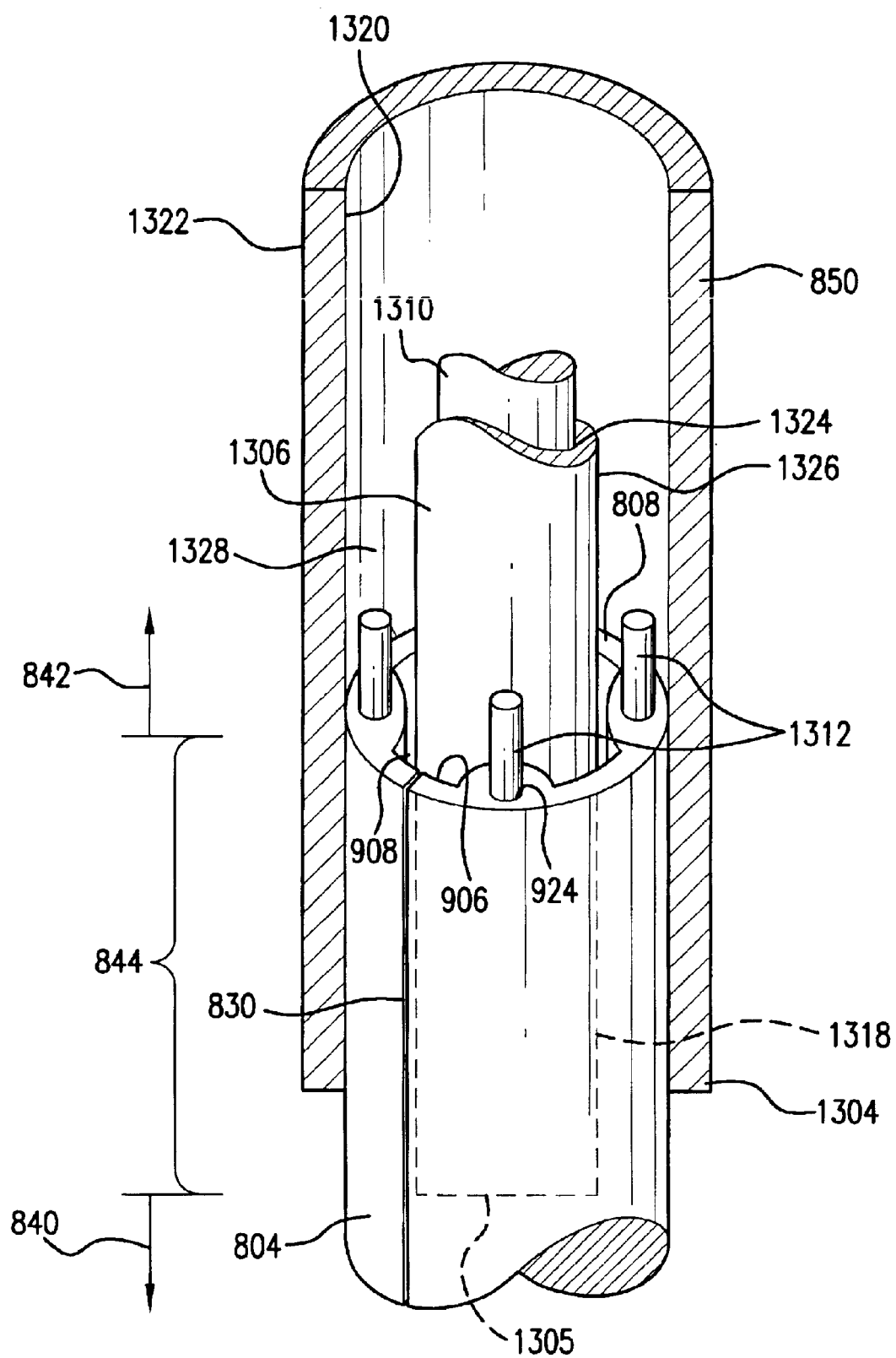
FIG. 13 is a perspective view of a portion 1300 of the balloon catheter of FIG. 8, including mandrels used to form the bond between a distal catheter section and a proximal catheter shaft according to the present invention.

FIG. 13 is a perspective view of a portion 1300 of the balloon catheter of FIG. 8. FIG. 13 shows how distal region 842 and proximal region 840 are bonded together in bond region 844. Bond region 844 is essentially where distal end 808 of proximal catheter shaft 804 is bonded to a proximal end 1304 of distal catheter shaft 850 and to a proximal end 1305 of distal guidewire shaft 1306. In order to better view the attachment of distal region 842 and proximal region 840, distal catheter shaft 850 is shown in cross-section. Proximal catheter shaft 804 is the same catheter shaft shown and described above with reference to FIG. 9, except that proximal catheter shaft 804 has only four nodes. However, as would be apparent to one skilled in the relevant art, the catheter shaft of FIGS. 4, 5 or 11 or another embodiment could also be assembled using the same method and technique.

Distal catheter shaft 850 includes proximal end 1304 and distal end (not shown) and an interior surface 1320 and an exterior surface 1322. Distal end 808 of proximal catheter shaft 804 extends into proximal end 1304 of distal catheter shaft 850. Proximal end 1305 of distal guidewire shaft 1306 extends into distal end 808 of proximal catheter shaft 804, as shown by the dashed lines 1318, such that distal guidewire shaft 1306 is coaxial with guidewire lumen 908 of proximal catheter shaft 804. Distal guidewire shaft 1306 extends from distal end 808 of proximal catheter shaft 804, through distal catheter shaft 850, and out the distal end of balloon 812 (not shown). Distal guidewire shaft 1306 also has an interior surface 1324 and an exterior surface 1326. The area between interior surface 1320 of distal catheter shaft 850 and exterior surface 1326 of distal guidewire shaft 1306 forms an annular shaped inflation lumen 1328 which is in open fluid communication with inflation lumen(s) 924 of proximal catheter shaft 804.

Both distal guidewire shaft 1306 and distal catheter shaft 850 are tubes and are formed of either the same or different material as proximal catheter shaft 804. Further, distal guidewire shaft 1306 should be comprised of a material that is easily bonded to proximal catheter shaft 804 and balloon 812.

Because distal guidewire shaft 1306 and distal catheter shaft 850 are bonded to proximal catheter shaft 804, much of the telescoping (i.e., one moving without the other) is reduced. The nodes 912 of proximal catheter shaft 804, keep distal guidewire shaft 1306 centered in distal catheter shaft 850.

For ease of manufacturing, a guidewire mandrel 1310 is shown disposed within distal guidewire shaft 1306. Additional inflation lumen mandrels 1312 are shown disposed in inflation lumen(s) 924 of proximal catheter shaft 804. Similar to the mandrels 610 and 612 as described above with respect to FIG. 6, the mandrels 1310, 1312 are inserted to maintain the lumens so that they do not become occluded by the melting materials used to create the bond between proximal catheter shaft 804 and distal guidewire shaft 1306, and between proximal catheter shaft 804 and distal catheter shaft 850. After the bonding process is complete, inflation lumen mandrels 1312 and guidewire mandrel 1310 are withdrawn, leaving open passages.

Any of the methods discussed above with respect to FIG. 6 may also be used to bond proximal catheter shaft 804 to distal catheter shaft 850 and distal guidewire shaft 1306. For example, a laser welding unit may melt exterior surface 1326 of distal guidewire shaft 1306 to interior wall surface 906 of proximal catheter shaft 804. Also, the laser welding unit may melt interior wall surface 1320 of distal catheter shaft 850 to exterior wall surface 904 of proximal catheter shaft 804 within bond region 844. Dilatation balloon 812 may then be bonded to exterior surface 1322 of distal catheter shaft 850 (not shown).

Figure 7:
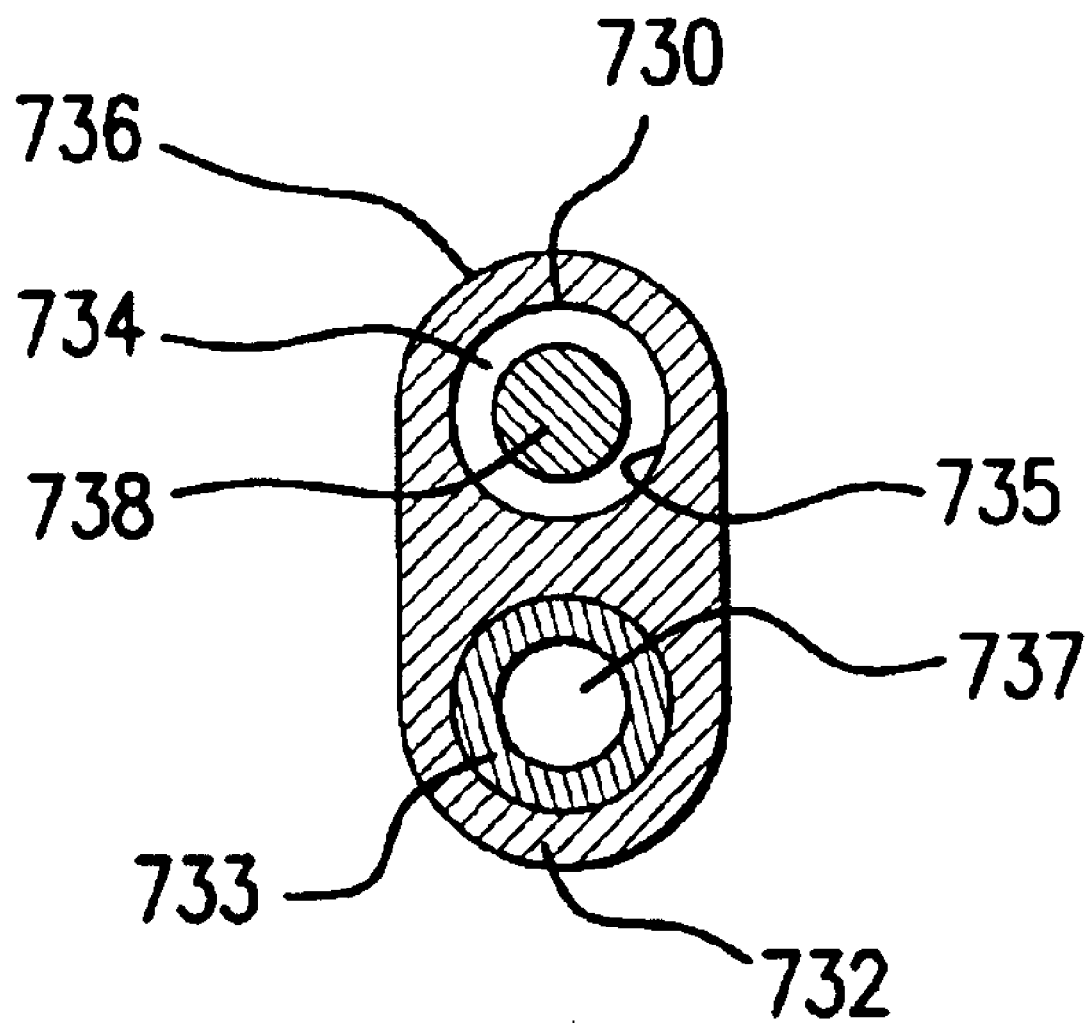
FIG. 7 is a cross-sectional view of a dual-lumen non-coaxial MX catheter.

The embodiment of FIG. 13 shows that cut 830 does not extend past proximal region 840. Therefore, preferably, distal region 842 begins just proximal of balloon 812 so that dilatation catheter 800 is easily exchanged. In an alternate embodiment, however, dilatation catheter 800 may not include distal catheter shaft 850 and guidewire shaft 1306. Thus, distal end 808 of proximal catheter shaft 804 (and therefore cut 830) may extend distally all the way to dilatation balloon 812, similar to that shown with respect to distal end 308 of the catheter shaft 304 of FIG. 3. Further, distal end 808 of proximal catheter shaft 804 maybe bonded to balloon 812 as discussed above with respect to FIG. 6. In yet another embodiment, distal region 842 may be formed from a non-coaxial extruded shaft, such as an MX catheter, as shown in FIG. 7. Thus, cut 830 may be extended into distal region 842.

The catheter shafts and guidewire lumens of the present invention can be manufactured using a number of different extruding methods. One method includes use of two extruders of typical design and configuration that feed a single extruder head or die. The extruders maybe of known design such as screw extruders using, for instance, screws typically chosen for the polymers employed in the catheter body. Each of the extruders have control valves which may be operated either as proportional valves or as cut-off valves.

Raw material is placed in each extruder. In one embodiment, the materials used are different materials. For instance, the material that will form the outer layer of the catheter shaft could be comprised of a first polymeric material which has greater strength than a second polymeric material which comprises the crowns on the inner portions of the catheter shaft. In one embodiment, the second polymeric material which comprises the crowns on the inner portions has frictional properties which facilitate guidewire passage and control.

The control valves regulate the flow of the polymer to the extruder, which melts the polymer to a semi-molten state. The polymers from each extruder enter the extruder head and exit through a die face. Pressurized air is also independently supplied to the extruder head and exits through the die face for each lumen formed in the catheter body. The pressurized air flowing through the die face insures that the extruded tubing has lumens of predetermined diameter.

The first polymeric material exits the die face through an outer annular region and the second polymeric material exits the die face through an inner annular region, or through locations corresponding to the crowns, as would be apparent to one skilled in the relevant art. The semi-molten catheter body is then pulled through a water bath typically using a puller.

While the invention has been particularly shown and described with reference to preferred embodiments thereof, it will be understood by those skilled in the art that various changes in form and detail may be made therein without departing from the spirit and scope of the invention.

What is claimed is:

1. A catheter for insertion into a body lumen over a guidewire, comprising:
    a catheter shaft having a proximal end and a distal end and an interior surface and an exterior surface, said interior surface defining a non-circular guidewire lumen, said non-circular guidewire lumen defined by a plurality of alternating arms and nodes;
    said catheter shaft comprises a first material and a crown portion comprises a second material that is different from said first material;
    a cut extending between said interior surface and said exterior surface of said catheter shaft, said cut being disposed at an apex of one of said guidewire lumen arms, said apex positioned where a distance between said interior surface and said exterior surface of said catheter shaft is at a minimum; and
    a guide member, wherein said guide member opens and closes said cut such that when the catheter is tracked of a guidewire, the guidewire is removable from said guidewire lumen of said catheter shaft via said guide member.

2. The catheter of claim 1, wherein said second material has a lower coefficient of friction than said first material.

3. The catheter of claim 1, wherein said second material is high density polyethylene.

4. The catheter of claim 1, wherein said first material is nylon.

5. A catheter for insertion into a body lumen over a guidewire, comprising:

a catheter shaft having a proximal end and a distal end and an interior surface and an exterior surface, said interior surface defining a non-circular guidewire lumen, said non-circular guidewire lumen defined by a plurality of alternating arms and nodes;

a cut extending between said interior surface and said exterior surface of said catheter shaft, said cut being disposed at an apex of one of said guidewire lumen arms, said apex positioned where a distance between said interior surface and said exterior surface of said catheter shaft is at a minimum; and a guide member, wherein said guide member opens and closes said cut such that when the catheter is tracked of a guidewire, the guidewire is removable from said guidewire lumen of said catheter shaft via said guide member; and wherein said exterior surface of said catheter shaft includes a plurality of indentations, each of which inwardly extends towards one of said arms.

6. The catheter of claim 5, wherein said plurality of indentations provide open area between said exterior surface of said catheter shaft and a guide catheter when the catheter is inserted therein.

7. A catheter for insertion into a body lumen over a guidewire, comprising:

a catheter shaft having a proximal end and a distal end and an interior surface and an exterior surface, said interior surface defining a non-circular guidewire lumen, said non-circular guidewire lumen defined by a plurality of alternating arms and nodes;

a cut extending between said interior surface and said exterior surface of said catheter shaft, said cut being disposed at an apex of one of said guidewire lumen arms, said apex positioned where a distance between said interior surface and said exterior surface of said catheter shaft is at a minimum; and a guide member, wherein said guide member opens and closes said cut such that when the catheter is tracked of a guidewire, the guidewire is removable from said guidewire lumen of said catheter shaft via said guide member; and further comprising an inflation lumen extending and a coaxial catheter shaft attached to a distal end of said catheter shaft, said coaxial shaft defining a distal guidewire lumen surrounded by a distal inflation lumen, such that said distal guidewire lumen is in fluid communication with said non-circular guidewire lumen and said distal inflation lumen is in fluid communication with each said inflation lumen.

8. The catheter of claim 7, further comprising an inflatable balloon attached to said distal end of said coaxial catheter shaft such that said balloon is in fluid communication with said distal inflation lumen.

9. A catheter, comprising:

a distal section and a proximal section, said distal section having a distal catheter shaft and a distal guidewire shaft disposed coaxially within said catheter shaft, said distal catheter shaft having an interior surface and an exterior surface and said distal guidewire shaft having an interior surface and an exterior surface, wherein said interior of said distal guidewire shaft defines a distal guidewire lumen and a distance between said exterior surface of said guidewire shaft and said interior surface of said distal catheter shaft defines a distal inflation lumen, said proximal section having a proximal catheter shaft including an interior surface and an exterior surface, said interior surface having a plurality of alternating arms and nodes and defining a proximal guidewire lumen and having a proximal inflation lumen disposed within at least one of said nodes, said distal section being bonded to said proximal section, such that said distal guidewire lumen is in communication with said proximal guidewire lumen and said proximal inflation lumen is in fluid communication with said distal inflation lumen.

10. The catheter of claim 9, wherein said distal guidewire shaft has proximal and distal ends and said proximal guidewire lumen has proximal and distal ends, said proximal end of said distal guidewire shaft being inserted into said distal end of said proximal guidewire lumen, such that, where inserted, said exterior surface of said distal guidewire shaft is bonded to crowns of said nodes of said interior surface of said proximal catheter shaft.

11. The catheter of claim 9, wherein said distal catheter shaft has proximal and distal ends and wherein said proximal catheter shaft has proximal and distal ends, said distal end of said proximal catheter shaft is inserted into said proximal end of said distal catheter shaft, such that, where inserted, at least a portion of said exterior surface of said proximal catheter shaft is bonded to said interior surface of said distal catheter shaft.

12. The catheter of claim 9, wherein said distal section is shorter than said proximal section.

13. The catheter of claim 9, further comprising:

a cut extending between said interior surface and said exterior surface of said proximal catheter shaft, said cut being disposed at an apex of one of said arms, said apex positioned where a distance between said interior surface and exterior surface of said proximal catheter shaft is at a minimum; and a guide member, wherein said guide member opens and closes said cut such that, when the catheter is tracked over a guidewire, the guidewire is removable from said proximal guidewire lumen of said proximal catheter shaft via said guide member.

14. The catheter of claim 9, wherein said proximal catheter shaft comprises a first material and crowns of said nodes comprise a second material that is different from said first material.

15. The catheter of claim 14, wherein said second material has a lower coefficient of friction than said first material.

16. The catheter of claim 14, wherein said second material is high density polyethylene.

17. The catheter of claim 14, wherein said first material is one of nylon or PEBAX.

18. The catheter of claim 9, wherein said distal catheter shaft and said distal guidewire shaft comprise a first material and said proximal catheter shaft comprises a second material.

19. The catheter of claim 18, wherein said first material is PEBAX or nylon.

20. The catheter of claim 18, wherein said second material is high density polyethylene.

21. The catheter of claim 9, wherein said exterior surface of said proximal catheter shaft includes a plurality of indentations, each of which inwardly extends towards one of said arms.

22. The catheter of claim 21, wherein said plurality of indentations provide open area between said exterior surface of said proximal catheter shaft and a body lumen when the catheter is inserted therein.

23. The catheter of claim 9, further comprising an inflatable balloon attached to a distal end of said distal catheter shaft such that said balloon is in fluid communication with said distal inflation lumen.

24. The catheter of claim 9, wherein said proximal guidewire lumen is defined by three or more nodes.

* * * * *